(12) United States Patent
Limoni et al.

(10) Patent No.: US 9,254,179 B2
(45) Date of Patent: Feb. 9, 2016

(54) SURGICAL SUPPORT SYSTEM

(71) Applicants: BAYCARE CLINIC, LLP., Green Bay, WI (US); FUSED INNOVATION, LLC., Neenah, WI (US)

(72) Inventors: Robert P. Limoni, Green Bay, WI (US); David Kettner, Greenville, WI (US)

(73) Assignees: Baycare Clinic, LLP, Green Bay, WI (US); Fused Innovation, LLC, Neenah, WI (US)

( * ) Notice: Subject to any disclaimer, the term of this patent is extended or adjusted under 35 U.S.C. 154(b) by 0 days.

(21) Appl. No.: 14/255,131

(22) Filed: Apr. 17, 2014

(65) Prior Publication Data

US 2015/0297302 A1 Oct. 22, 2015

(51) Int. Cl.

| | |
|---|---|
| *E04G 3/00* | (2006.01) |
| *A61B 19/00* | (2006.01) |
| *A61G 13/12* | (2006.01) |
| *F16M 13/00* | (2006.01) |

(52) U.S. Cl.
CPC ............. *A61B 19/26* (2013.01); *A61G 13/125* (2013.01); *F16M 13/00* (2013.01); *A61B 2019/267* (2013.01)

(58) Field of Classification Search
CPC ............. A61B 19/26; A61B 2019/267; A61G 13/125; F16M 13/00
See application file for complete search history.

(56) References Cited

U.S. PATENT DOCUMENTS

| | | | |
|---|---|---|---|
| 3,753,557 A | 8/1973 | Kelley | |
| 4,136,858 A | 1/1979 | Petersen | |
| 4,545,573 A | 10/1985 | Murphy | |
| 4,615,516 A | 10/1986 | Stulberg et al. | |
| 4,730,609 A | 3/1988 | McConnell | |
| 4,913,413 A | 4/1990 | Raab | |
| 5,027,799 A | 7/1991 | Laico et al. | |
| 5,537,700 A | 7/1996 | Way et al. | |
| 6,471,172 B1 | 10/2002 | Lemke et al. | |
| 6,824,511 B1 * | 11/2004 | Bell et al. ...................... | 600/227 |
| 7,290,302 B2 | 11/2007 | Sharps | |
| 8,425,522 B2 | 4/2013 | Bonutti | |
| 8,434,491 B2 | 5/2013 | Born | |
| 9,044,269 B2 * | 6/2015 | Woerlein | |
| 2004/0133078 A1 * | 7/2004 | Edoga et al. .................. | 600/227 |
| 2005/0160533 A1 | 7/2005 | Boucher et al. | |
| 2007/0094798 A1 | 5/2007 | Yu | |
| 2012/0305005 A1 | 12/2012 | Keith-Lucas et al. | |
| 2012/0324650 A1 | 12/2012 | Russell | |

FOREIGN PATENT DOCUMENTS

| | | |
|---|---|---|
| EP | 0755659 A1 | 1/1997 |
| WO | 2013034916 A1 | 3/2013 |

OTHER PUBLICATIONS

International Search Report & Written Opinion; Int'l Application No. PCT/US2015/020714; May 27, 2015.

* cited by examiner

*Primary Examiner* — Shin Kim
(74) *Attorney, Agent, or Firm* — Boyle Fredrickson, S.C.

(57) ABSTRACT

A surgical support attaches to a surgical table by means of mounting plates and base plates that may communicate through a surgical drape without puncturing the surgical drape. The base plates may be attached to the surgical table by means of a pegboard or by direct clamping of the base plates to a side of the surgical table underneath the surgical drape.

21 Claims, 5 Drawing Sheets

SURGICAL SUPPORT SYSTEM

STATEMENT REGARDING FEDERALLY
SPONSORED RESEARCH OR DEVELOPMENT

CROSS REFERENCE TO RELATED
APPLICATION

BACKGROUND OF THE INVENTION

The present invention relates to a surgical support system for supporting a surgical device or patient during surgery and in particular to a support system that can be attached to and adjusted with respect to the operating table from the sterile operating field through a surgical drape.

During surgery, a surgical drape may be placed ova the operating table to isolate a sterile operating area and sterile equipment from non-sterile areas and equipment. The surgical drape is typically a disposable, flexible plastic material.

For surgical procedures such as a total knee replacement, it is necessary for the patient's leg to be properly positioned and then held fixed in that position before cuts are made for the removal of the existing joint. For this purpose, a sterile leg support system may be positioned on the sterile side of the surgical drape.

Such support systems often compromise the sterile barrier of the surgical drape by going around it to the side or penetrating the surgical drape. Some systems attempt to clamp a support system over top of the sterile barrier, but nearly always penetrate the surgical drape. An adhesive backed covering applied to the sterile drape may be used to minimize the opening formed in the surgical drape when the surgical drape is cut or punctured, but such covering has only limited success in preventing contamination of the sterile field. Substantial adjustment of such patient support fixtures, as may be necessary for proper surgery, often requires the physician to move between the sterile and non-sterile fields jeopardizing the sterility of the sterile field.

SUMMARY OF THE INVENTION

The present invention provides a t fixture that may be repositioned and fixed with respect to the operating table through the surgical drape without penetration of the surgical drape. This is accomplished generally by mechanically interlocking elements that gently deform the surgical drape while engaging each other. Forces of torsion or shear forces along the plane of the table are resisted by abutting surfaces of the interlocking elements when they are engaged. A very light latching force (for example from a magnet system) prevents inadvertent disengagement of the interlocking elements.

Specifically, the present invention generally provides a surgical support system for use with an operating room table having a surface defining a table plane. The surgical support system includes at least one base element fixable with respect to the operating room table to extend along the table plane and to present first mechanical interlock features exposed on a upper surface of the base element away from the table top surface A corresponding mounting element then provides second mechanical interlock features interengagable with the first mechanical interlock features of the base element through a pliable surgical drape material without breech of the surgical drape material, where the interlocking of the first and second mechanical interlock features through the surgical drape block relative movement of the base element and the mounting plate along the table plane while allowing engagement and disengagement of the base element and the mounting element along a direction generally perpendicular to the table plane. Latch components are positioned on the base element and mounting element to releasably retain the base element and mounting element against disengagement of the base element and mounting element along a direction generally perpendicular to the table plane. At least one attachment feature is also provided on the upper surface of the mounting element to retain a surgical device such as a patient support or robot am during surgery.

It is thus a feature of at least one embodiment of the invention to provide a surgical support system that interlocks through the sterile drape eliminating the need for the surgeon to move between non-sterile and sterile areas in positioning a patient support.

The blocking of relative movement of the base element and mounting plate may be provided by surfaces that abut through the surgical drape along a line substantially perpendicular to the table plane.

It is thus a feature of at least one embodiment of the invention to provide a method of stabilizing a support used for compression or traction forces by a simple mechanical abutment which tends to compress rather than tear the surgical drape.

The first and second mechanical interlock elements may be inter-engaging pegs and sockets sized to engage through a surgical drape.

It is thus a feature of at least one embodiment of the invention to provide a system that allows forces to be spread over many contact areas that each requires only minor distention of the surgical drape.

The pegs and sockets provide rounded edges to avoid cutting of the surgical drape.

It is thus a feature of at least one embodiment of the invention to reduce force-concentrating surfaces that might tear or thin the surgical drape.

The latch components may be opposed magnetically attractable materials mounted in opposition on the base element and mounting element.

It is thus a feature of at least one embodiment of the invention to provide a simple releasable mechanism that may work through the separation of the surgical drape.

The magnetically attractable materials may be selected from permanent magnet material and ferromagnetic material.

It is thus a feature of at least one embodiment of the invention to permit a combination of magnets or magnets and ferromagnetic materials to provide flexible trade-off between cost and attractive force.

The base element and mounting element may include at least three abutting surfaces separated by at least one inch to define a plane of contact when the first and second mechanical interlock elements are engaged.

It is thus a feature of at least one embodiment of the invention to provide a stable mounting surface resistant to tipping under shear forces.

The first and second mechanical interlock elements may block relative twisting of the base element with respect to the mounting element about an axis generally normal to the table plane when the first and second mechanical interlock features are engaged.

It is a further feature of at least one embodiment of the invention to provide a mounting surface resistant to torsion about a vertical axis.

The mounting element may include an undercut edge for receiving a user's fingers to lift the mounting edge away from the table.

It is thus a feature of at least one embodiment of the invention to allow ready removal and reattachment of the mounting element, for example, by a surgeon having gloved hands.

The base element and mounting element and first and second mechanical interlock features may be a metal such as aluminum or stainless steel It is thus a feature of at least one embodiment of the invention to provide a sterilizable material that provides sufficient strength and may readily be fabricated into the necessary interlocking shapes.

The surgical support system may further include a table plate fixable with respect to the operating room table and having periodic third mechanical interlock features engageable at periodic locations with fourth mechanical interlock features exposed at a lower surface of the base element toward the table top surface so that the base element may be located at any of the periodic locations to be fixed with respect to the operating room table.

It is thus a feature of at least one embodiment of the invention to permit a "pegboard" type arrangement that allows a larger range of repositioning of the mounting elements at regular locations from within the sterile field.

The third and fourth mechanical interlock features engage at either of two perpendicular angles about an axis normal to the table plane.

It is thus a feature of at least one embodiment of the invention to permit translational and rotational repositioning after the surgical drape is in position.

Alternatively, the base element includes a clamp bar to be attached to a clamp of the operating room table to fix the base element with respect to the operating room table.

It is thus a feature of at least one embodiment of the invention to provide a simple mechanism for attaching the base elements to the table making use of the standard clamp system available on surgical tables.

The attachment feature of the mounting element may be an upwardly extending cylindrical peg.

It is thus a feature of at least one embodiment of the invention to provide a mounting element that may be engaged and disengaged in a direction generally perpendicular to the intended compression or traction forces and which allows ready angular adjustment.

The surgical support system may further include a patient support fixture releasably attachable to the mounting element.

It is thus a feature of at least one embodiment of the invention to provide a patient fixture to be positioned and/or attached within the sterile field during surgery.

The support fixture may be a foot stirrup.

It is thus a feature of at least one embodiment of the invention to provide a patient fixture suitable for knee surgery and the like.

The support fixture may further include a beam pivoting at a first end with respect to at least one mounting element and swinging at a second end across an index surface with respect to at least one mounting element, the second end releasably lockable to the index surface at a plurality of angles. A lockable slide is positioned to be movable along the beam and releasably lockable to the beam at a plurality of positions along the beam and a foot stirrup is attached to the lockable slide for receiving and supporting a human foot therein.

It is thus a feature of at least one embodiment of the invention to provide a patient fixture suitable for knee surgery that allows multiple dimensions of adjustment from within the sterile field.

The foot stirrup may be pivotably attached to the lockable slide about an axis generally perpendicular to an extent of the beam.

It is thus a feature of at least one embodiment of the invention to accommodate different extensions of the patient's leg while preserving natural ankle position.

These particular objects and advantages may apply to only some embodiments falling within the claims and thus do not define the scope of the invention.

DETAILED DESCRIPTION OF THE PREFERRED EMBODIMENT

Figure 1:
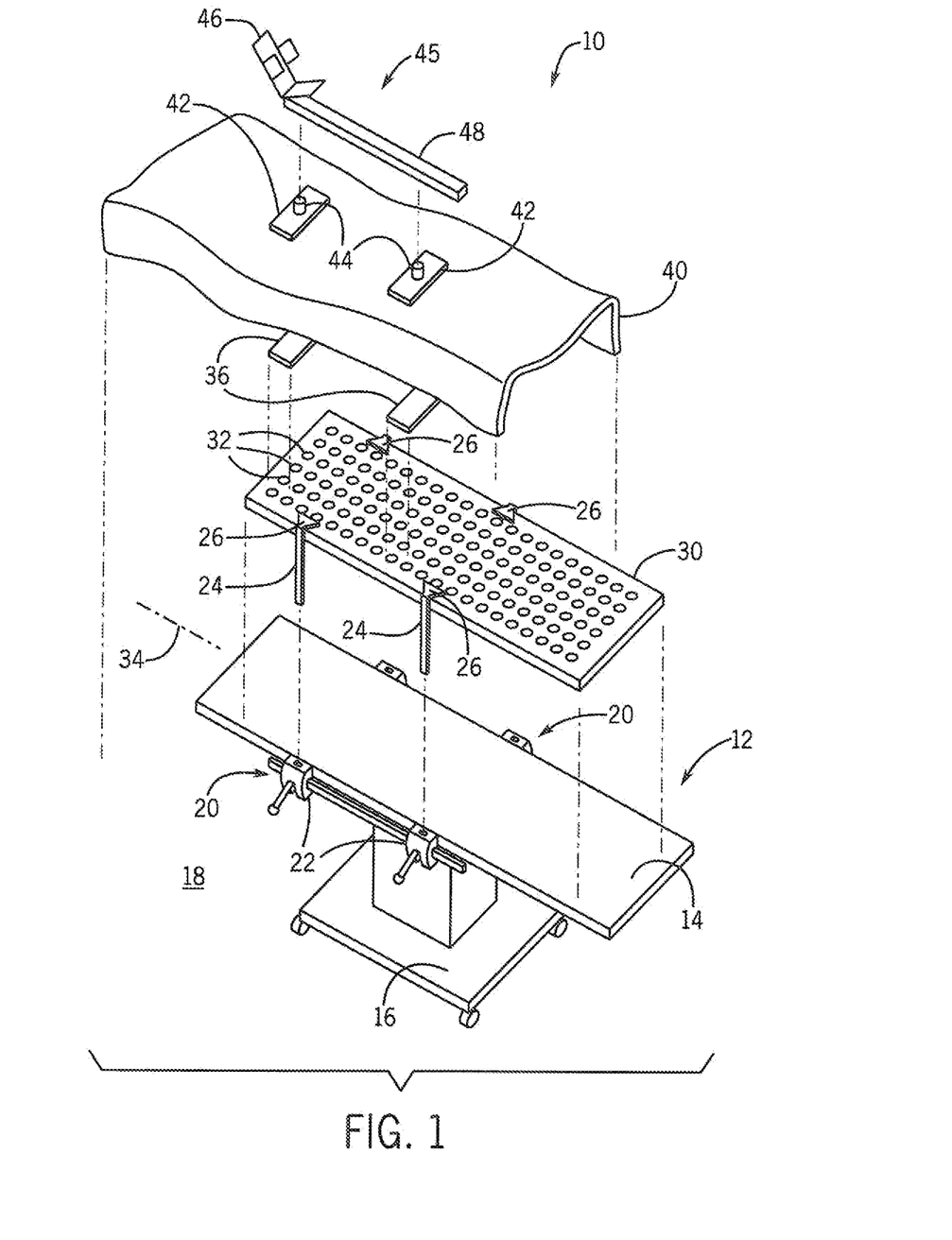
FIG. 1 is an exploded perspective view of an operating room table fit with a "pegboard" holding multiple base plates that may engage through a surgical drape with mounting plates attached to a patient support fixture.

Referring now to FIG. 1, a surgical support system 10 may work in conjunction with a standard surgery table 12 of the type providing a generally horizontal table top surface 14 supported on a pedestal 16 with respect to the floor surface 18 or the like. The surgery table 12 may include universal side mounting rails 20 the type generally understood in the art having positionable clamps 22 located on either side of the table top surface 14.

Generally the clamps 22 are positioned slightly below the table top surface 14 to receive vertically extending clamp bars 24 of clamp fixtures 26 or the like. The clamps 22 may be tightened to retain the clamp bars 24 in a desired position with respect to vertical height and longitudinal location along the side of the table top surface 14.

In a first embodiment of the invention, clamp fixtures 26 are positioned and adjusted to attach a "pegboard" 30 to overlie all or a portion of the table top surface 14. Generally the pegboard 30 may be a molded or machined rigid plastic material, for example, approximately ¾ of an inch thick. A set of holes 32 of approximately 1 inch in diameter may be spaced periodically at intersections in a rectilinear grid oriented diagonally with respect to a longitudinal axis 34 of the surgery table 12.

One or more base plates 36 may be installed on top of the pegboard 30 and retained there by downwardly extending cylindrical knobs 66 (shown in FIG. 3) that fit within corresponding holes 32. In a preferred embodiment, the base plates 36 are generally rectangular plates 3½ inches by 8 inches and about one quarter inch thick and constructed of a metal such as aluminum or stainless steel machined or otherwise formed as is understood in the art. The invention also contemplates manufacture of these elements from reinforced thermoplastic materials. Generally, the pattern of downwardly extending cylindrical knobs 66 in the base plate 36 and holes 32 in the pegboard 30 allows the base plates 36 to be placed in either of two perpendicular positions, either with a longest extent of the base plate 36 aligned with longitudinal axis 34 or perpendicular to a longitudinal axis 34 along the transverse axis, and allows the base plates 36 to be moved incrementally longitudinally or transversely by the periodicity of the holes 32 or approximately 3 inches along each grid axis.

A surgical drape 40 may be placed over the table top surface 14 and pegboard 30 with its attached base plates 36. The surgical drape 40 is generally a water-impervious flexible plastic sheet (for example polyethylene) 1-10 mils in thickness and may include a water-absorbent upper layer. Mounting plates 42 having similar dimension to base plates 36 may then be attached to the base plates 36 through the surgical drape 40 without perforation of the surgical drape 40 as will be discussed below.

A cylindrical attachment pin 44 extends upward from the center of the mounting plate 42 to allow the mounting plate 42 to attach to a patient fixture 45, in this case, the patient fixture 45 providing a foot stirrup 46 mounted on a rail 48, the latter of which may attach to two of the mounting plates 42 with each mounting plate 42 extending transversely.

Figure 2:
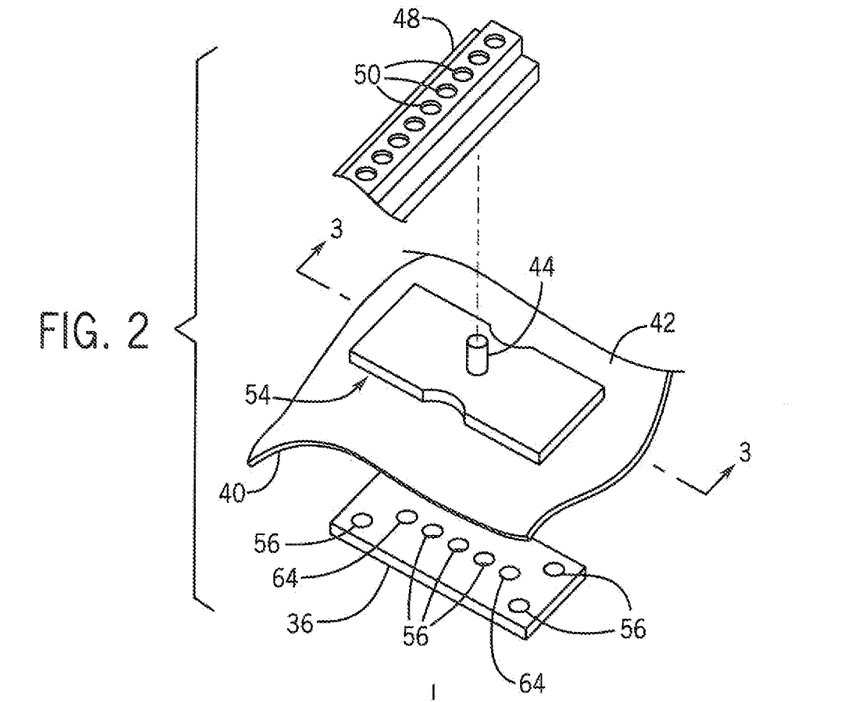
FIG. 2 is a fragmentary exploded perspective view of a support rail of the patient fixture as may be connected to an attachment feature on a mounting plate and showing the mounting plate positioned opposite a base plate with which it engages through a surgical drape.

Referring now to FIG. 2, the rail 48 may include a series of regularly spaced vertical bores 50 separated along its length and each sized to receive the cylindrical attachment pin 44 extending up from the mounting plate 42. The cylindrical attachment pin 44 may be slightly conical so as to provide a wedge fit with the bores 50 when the two are pressed together.

Figure 3:
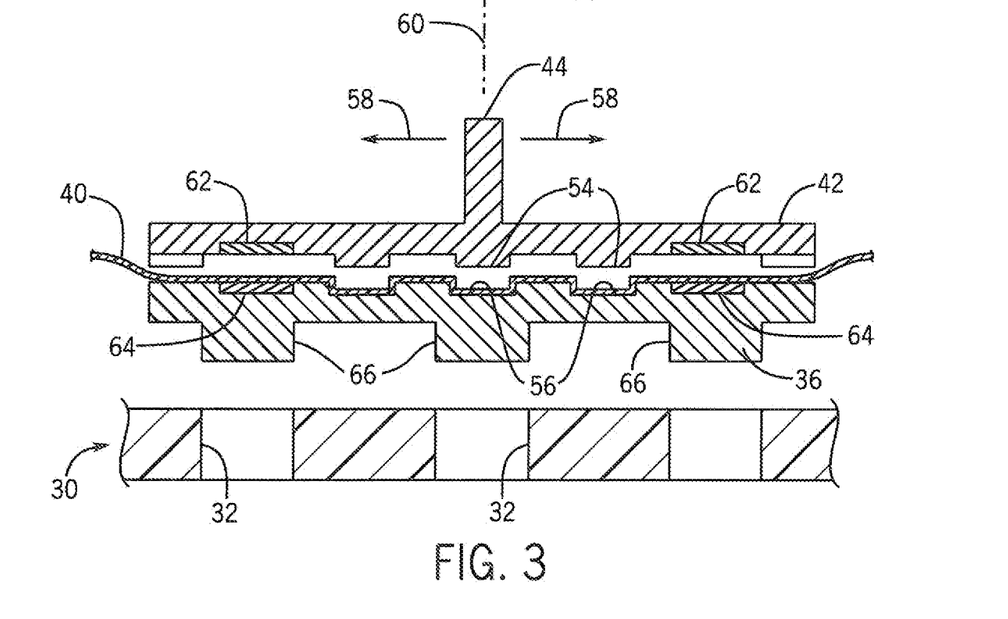
FIG. 3 is a cross-sectional view along lines 3-3 of FIG. 2 showing inter-engaging mechanical elements of pegs and sockets that may operate through the surgical drape between the mounting plate and the base plate and the engagement of downwardly extending cylindrical knobs of the base plate engaging with holes in the pegboard.

Referring also to FIG. 3, the upper surface of the mounting plate 42 may otherwise be substantially planar of similar dimensions to the base plate 36 to provide a surface against which the bottom of the rail 48 may stably rest. The lower surface of the mounting plate 42 may provide for a set of downwardly extending pegs 54 that may be received within corresponding upwardly open blinded sockets 56 in the upper surface of the base plate 36. In one embodiment, four pegs 54 and four corresponding sockets 56 are placed in the corners of each of the mounting plate 42 and base plate 36, respectively, and three pegs 54 and sockets 56 are placed along a center of its longest axis of each of the mounting plate 42 and base plates 36, respectively.

The size of the pegs 54 is slightly smaller than the sockets 56 so as to accommodate the thickness of the surgical drape 40 therebetween without substantial distention or tearing of the surgical drape 40. Abutment of the sidewalks of the pegs 54 and sockets 56 substantially resist shear movement 58 of the mounting plate 42 with respect to the base plate 36 along the plane of the table top surface 14, as resisted by the inter-engaging of the substantially vertical walls of the pegs 54 and sockets 56 through the surgical drape 40. Similarly, the mounting plate 42 resists torsion about a vertical axis 60, for example, through cylindrical attachment pin 44 by inter-engaging of these substantially vertical walls. In one embodiment a total of seven pegs 54 and seven sockets 56 will be engaged with at least three of the inter-engaging pegs 54 and sockets 56 separated by more than one inch from each of the others along the plane of the table top surface 14.

The pegs 54 may be substantially cylindrical with rounded bases to avoid sharp edges that might cut or tear the surgical drape 40. Generally the pegs 54 will have a height of approximately one-quarter inch equal to the corresponding height of the sockets 56. In an alternative embodiment (not depicted), the pegs 54 may be radially asymmetric, having polygonal or T cross-sections that serve to resist torsion about the vertical axis 60 with or without other adjacent pegs 54. In this case, the sockets 56 conform in outline to the cross-sections of the pegs 54.

Outside the region of the pegs 54 and sockets 56, the mounting plate 42 and base plate 36 abut over substantially planar surfaces of greater than four square inches. The mounting plate 42 and base plate 36 may be formed of a cast or machined metal such as aluminum or stainless steel or molded from a rigid thermoplastic material.

The mounting plate 42 and base plate 36 may be retained together about the surgical drape 40 against disengaging resilience of the surgical drape 40 and/or any slight upward jarring on the mounting plate 42 by means of magnetic attraction between magnetically attractive materials 62 inset in the lower surface of the base plate 36 across from magnetically attractive materials 64 inset into the upper surface of the base plate 36. These magnetically attractive materials 62 and 64 may be each permanent magnets oriented to have opposed, and hence attracting, north and south poles or one permanent magnet and one ferromagnetic material such as a steel or iron plate. It will be appreciated that the force of magnetic attraction needs to serve only to preserve engagement of the mounting plate 42 and base plate 36 against relatively minor forces and needs not to resist substantial shear forces 58 or torsional forces necessary for traction or compression which are handled by mechanical inter-engagement of the pegs 54 and sockets 56.

Referring still to FIG. 3, the lower surface of the base plate 36 base provides substantially larger cylindrical knobs 66 received within holes 32 in the pegboard 30 which may resist accidental disengagement simply by their greater height (approximately ¾ of an inch) of engagement as well as a slight downwardly narrowing conical to the cylindrical knobs 66 which serve to wedge them into the holes 32 by interference fit.

It will be appreciated that the abutting planar surface of the mounting plate 42 and the base plate 36 surrounding the interlocking features of the pegs 54 and sockets 56 provide primary supporting contact surface on alternate sides of the surgical drape 40. These surfaces serve to capture the drape material peripherally around the interlocking features preventing movement in the drape material, from inducing stress on the drape material at the engagement site of the interlocking features.

Figure 4:
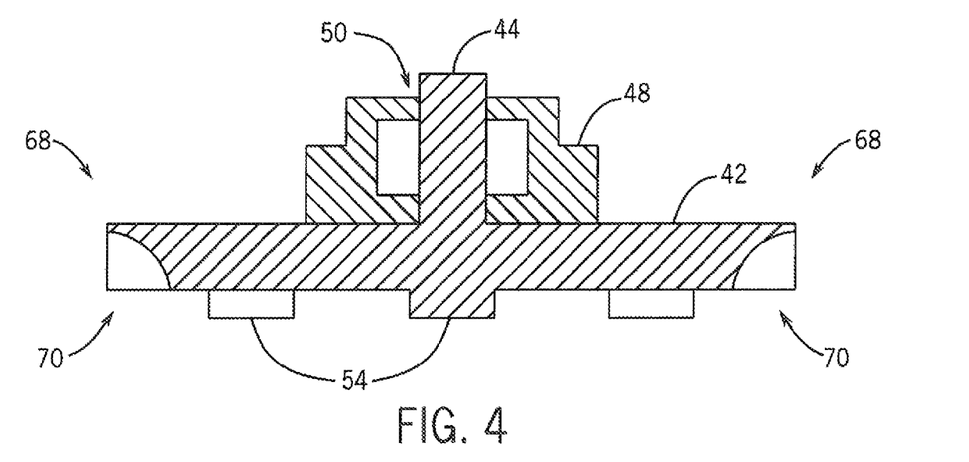
FIG. 4 is a cross-sectional view perpendicular to that of FIG. 3 of the support beam as attached to the mounting plate and showing undercuts for removal of the mounting plate.

Referring now to FIG. 4, transverse edges 68 of the mounting plate 42 may include undercut portions 70 that may receive a user's fingers to help pry the mounting plate 42 away from the base plate 36 (not shown in FIG. 4) without tearing or gouging of the surgical drape 40.

It will be appreciated that the elements of the mounting plate 42 may be alternatively manufactured from other materials such as stainless steel, aluminum, titanium, or carbon fiber composites that can withstand high-temperature environments in the sterilization process.

It will be further appreciated that in an alternative embodiment, the pegs 54 may be sized to be received directly by holes 32 in the pegboard 30 to allow greater flexibility in the positioning or repositioning of the mounting plates 42 during surgery. In this case magnetically attractive material 64 may be regularly embedded in the pegboard 30, for example, steel discs or the like.

Figure 5:
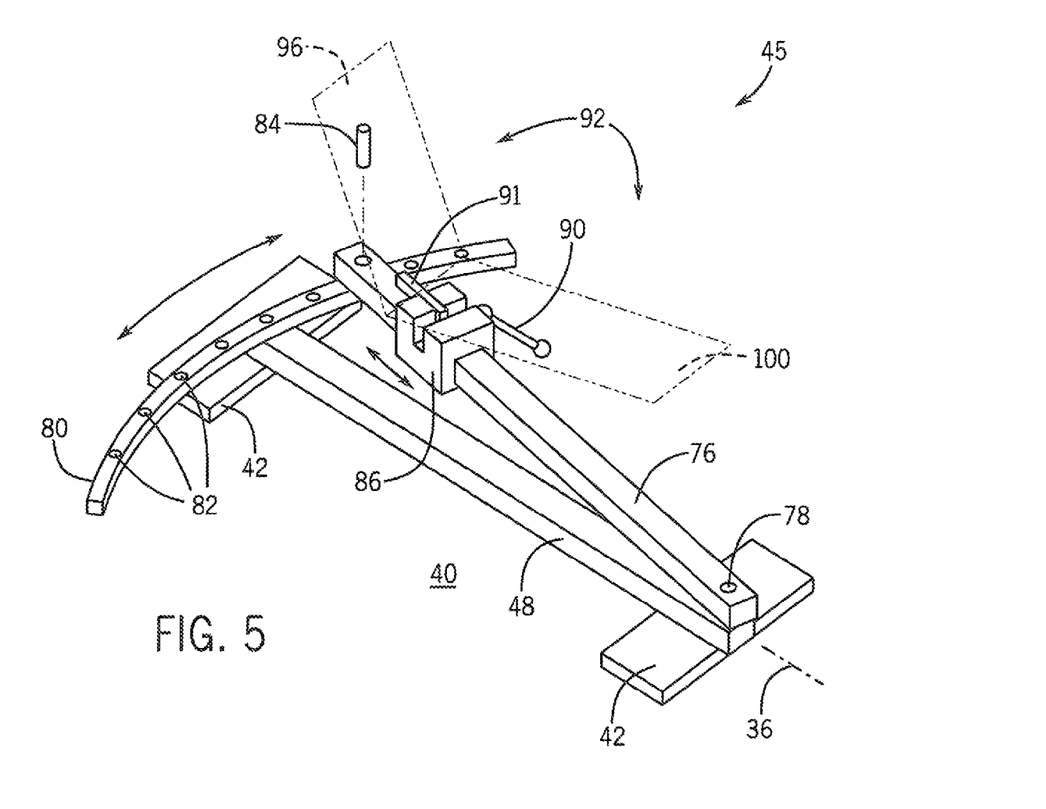
FIG. 5 is a perspective view in partial phantom of a more sophisticated patient support fixture as attached to two mounting plates such as provide for an angulation and extension adjustment.

Referring now to FIG. 5, two mounting plates 42 may be placed on the surgical drape 40 to support a rail 48 at its opposite ends, the rail 48 extending generally along the longitudinal axis 34. It will be understood that base plates 36 have been placed beneath the surgical drape 40 to support the mounting plates 42 as required. An elongated swing arm 76 may be attached to a superior end of the rail 48 at a vertical pivot 78 so that the opposite end of the swing arm 76 may slide along a radiused index surface 80 to multiple different angular positions each aligned with an upwardly extending index hole 82 in the index surface 80. The angular range of sliding will typically be greater than 20 degrees and may be, for example, 24 degrees. A pin 84 passing vertically through the movable end of the swing arm 76 to be received by an index hole 82 may fix the swing arm 76 at any of a variety of different angular positions. A slide 86 fits over the swing arm 76 to slide to a variety of different positions along the swing arm 76 and then lock in any of those positions by lock arm 90.

Figure 6:
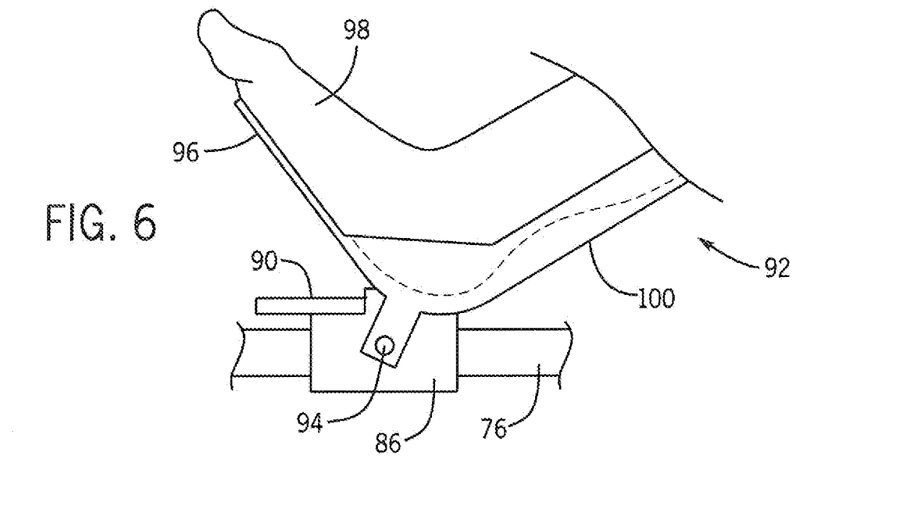
FIG. 6 is a fragmentary side elevational view of the patient's foot in a foot stirrup of the fixture of FIG. 5.

Referring also to FIG. 6, a foot stirrup 92 may be pivotally attached to the top of the slide 86 through horizontal pivot 94 that may also be locked as will be described below. The foot stirrup 92 includes a sole plate 96 supporting a sole of a patient's foot 98 and a calf support 100 supporting the patient's calf. It will be appreciated that by adjustment of the angle of the swing arm 76, the position of the slide 86 on the swing arm 76, and the angle of the foot stirrup 92, adjustment of the patient's leg may be had in these three different dimensions for proper angulation the hip and the knee joint. For this purpose, pivot point 78 may be positioned to be close to the patient's hip joint Referring now to FIG. 7, in an alternative embodiment, base plates 36, for example, appropriate for the support of the patient fixture 45 shown in FIG. 5 may be attached directly to clamp bars 24 to be received by clamps 22 without the need for the pegboard 30 while also preserving the segregation between the mounting plates 42 on the sterile side of the surgical drape 40 and the base plates 36 on the non-sterile side.

Figure 8A:
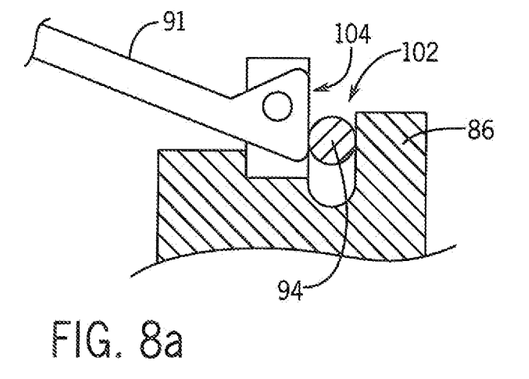
FIGS. 8*a* and 8*b* are fragmentary cross-sections of a mounting slide for the foot stirrup of FIG. 6 that automatically locks to a pivot element of the foot stirrup when the foot stirrup is attached to the mounting slide.
Figure 8B:
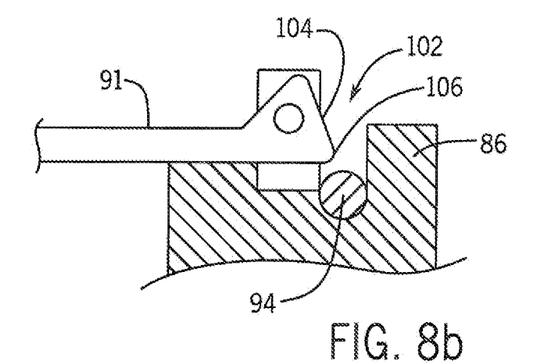

Referring now to FIGS. 8a and 8b the slide 86 may have an upwardly opening transverse notch 102 that may receive the horizontal pivot 94 of the foot stirrup 92 (shown in FIGS. 5 and 6). Lock arm 91 provides a cam surface 104 that raises the locking lever 91 as the pivot 94 passes downward into the notch 102 when the foot stirrup is engaged with the slide 86 as shown in FIG. 8a. Referring to FIG. 8b, when the horizontal pivot 94 is fully seated at the bottom of the notch 102, the cam surface 104 no longer contacts the pivot 94 and the lock arm 91 drops so that a protruding portion 106 of the cam surface 104 blocks upward movement of the horizontal pivot 94 until the lock arm is manually raised in this way, the surgeon can easily install the foot stirrup 92 single-handedly with it automatically locking in position yet still able to pivot.

Figure 7:
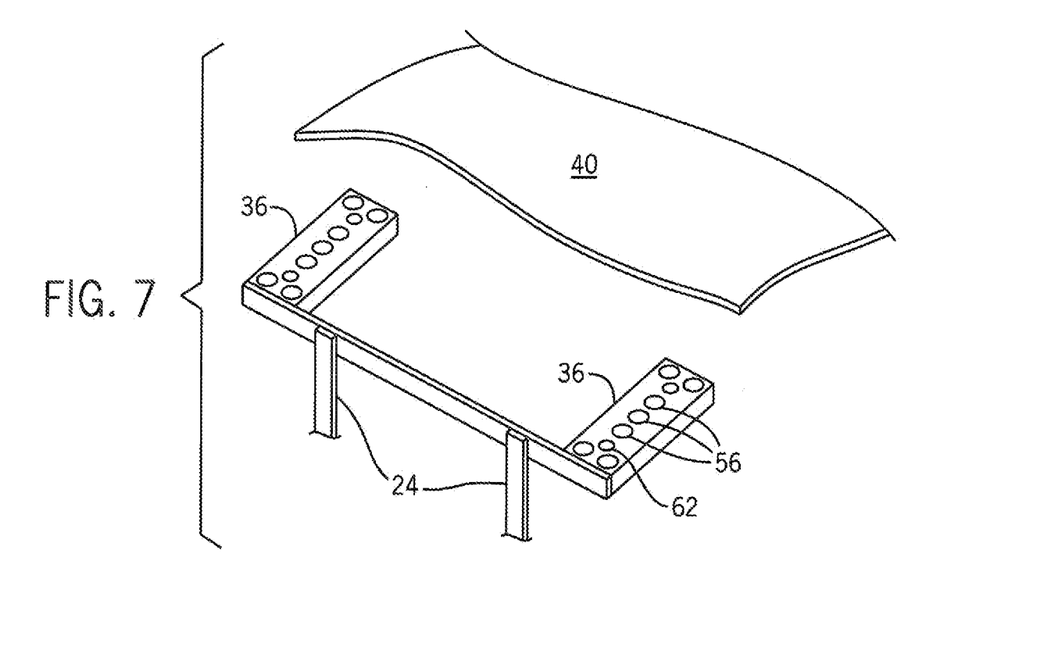
FIG. 7 is a perspective view of an alternative assembly of base plates to a patient table not requiring the pegboard of FIG. 1 but attached directly to universal side rails of the patient table.
Figure 9:
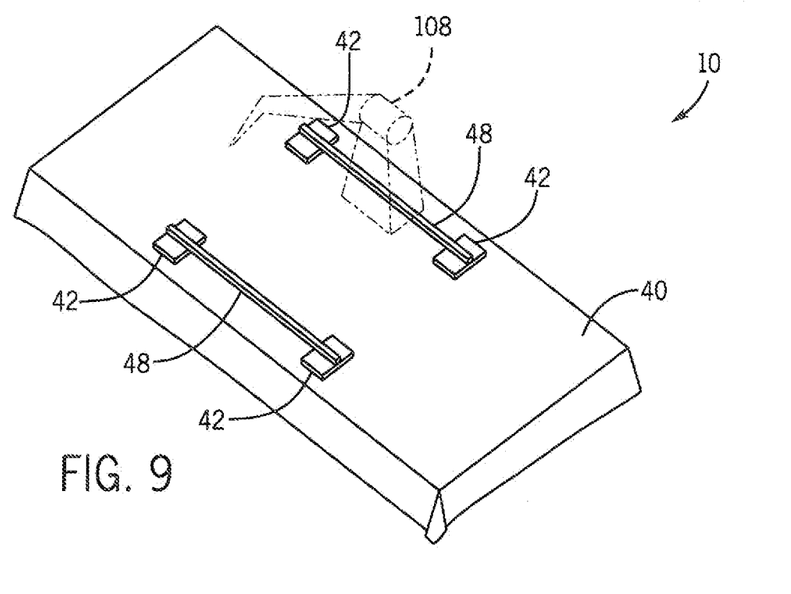
FIG. 9 is a figure similar to that of FIG. 1 showing the mounting plates assembled over a surgical drape and used for mounting an arbitrary surgical device such as a robot arm.

Referring now to FIG. 9, it will be appreciated that the present fixturing system may be used for a variety of surgical accessories not limited to patient positioning elements. For example, a surgical device 108 such as a surgical robot arm or the like may be attached to the rail 48 to allow it to be placed in close proximity to the patient yet at a known location accurately fixed with respect, for example, to the underlying pegboard 30 (shown in FIG. 1) or otherwise positioned mounting plates 36 (such as shown in FIG. 7). By employing the system of the present invention, the surgical device 108 may be rapidly repositioned, for example, on a second rail 48 to a known location with respect to its first position to take advantage previous effort in precisely locating the patient as stabilized on the table possibly by other implementations of the present invention. The surgical device 108 may be located and fixed to particular locations on the rail 48, determined, for example, by bores 50 (shown in FIG. 2) and/or may employ the rail 48 as an additional movement axis or indexing device through the use of an appropriate drive mechanism engaging the rail 48 or the like.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What we claim is:

1. A surgical support system for use with an operating room table having a surface defining a table plane, the surgical support system comprising:
   a base element fixable with respect to the operating room table to extend along the table plane and to present first mechanical interlock features exposed on an upper surface of the base element away from the table surface;
   a mounting element having second mechanical interlock features inter-engagable with the first mechanical interlock features of the base element through a pliable surgical drape material without breech of the surgical drape material, an interlocking of the first and second mechanical interlock features through the surgical drape blocking relative movement of the base element and the mounting element along the table plane while allowing engagement and disengagement of the base element and the mounting element along a direction generally perpendicular to the table plane;

latch components positioned on the base element and mounting element to releasably retain the base element and mounting element against disengagement of the base element and mounting element along a direction generally perpendicular to the table plane; and at least one attachment feature on an upper surface of the mounting element for retaining a surgical device during surgery.

2. The surgical support system of claim 1 wherein the blocking of relative movement of the base element and mounting plate is provided by surfaces that abut through the surgical drape along a line substantially perpendicular to the table plane.

3. The surgical support system of claim 2 wherein the first and second mechanical interlock elements are inter-engaging pegs and sockets sized to engage through a surgical drape.

4. The surgical support system of claim 3 wherein the pegs and sockets provide rounded edges to avoid cutting of the surgical drape.

5. The surgical support system of claim 2 wherein the latch components are opposed, magnetically-attractable materials mounted in opposition on the base element and mounting element.

6. The surgical support system of claim 5 wherein the magnetically attractable materials are selected from permanent magnet material and ferromagnetic material.

7. The surgical support system of claim 1 wherein the base element and mounting element include at least three abutting surfaces separated by at least one inch to define a plane of contact when the first and second mechanical interlock elements are engaged.

8. The surgical support system of claim 1 wherein the first and second mechanical interlock elements block relative twisting of the base element with respect to the mounting element about an axis generally normal to the table plane when the first and second mechanical interlock features are engaged.

9. The surgical support system of claim 1 wherein the mounting element includes an undercut edge for receiving a user's fingers to lift the mounting edge away from the table.

10. The surgical support system of claim 1 wherein the base element and mounting element and first and second mechanical interlock features are a metal selected from the group consisting of aluminum and stainless steel.

11. The surgical support system of claim 1 further including the pliable surgical drape material captured between the base element and mounting element.

12. The surgical support system of claim 1 further including a table plate fixable with respect to the operating room table and having periodic third mechanical interlock features engageable at periodic locations with fourth mechanical interlock features exposed at a lower surface of the base element toward the table surface so that the base element may be located at any of the periodic locations to be fixed with respect to the operating room table.

13. The surgical support system of claim 12 wherein the third and fourth mechanical interlock features engage at either of two perpendicular angles about an axis normal to the table plane.

14. The surgical support system of claim 1 wherein the base element includes a clamp bar to be attached to a clamp of the operating room table to fix the base element with respect to the operating room table.

15. The surgical support system of claim 1 wherein the attachment feature is an upwardly extending peg.

16. The surgical support system of claim 1 wherein the surgical device is a patient support fixture releasably attachable to the mounting element.

17. The surgical support system of claim 16 wherein the patient support fixture is a foot stirrup.

18. The surgical support system of claim 16 wherein the patient support fixture further includes:

a beam pivoting at a first end with respect to at least one mounting element and swinging at a second end across an index surface with respect to at least one mounting element, the second end releasably lockable to the index surface at a plurality of angles;

a lockable slide movable along the beam and releasably lockable to the beam at a plurality of positions along the beam; and a foot stirrup attached to the lockable slide for receiving and supporting a human foot therein.

19. The surgical support system of claim 18 wherein the foot stirrup is pivotably attached to the lockable slide about an axis generally perpendicular to an extent of the beam.

20. The surgical support system of claim 19 wherein the lockable slide provides a latch mechanism with a release operator receiving the foot stirrup and retaining the same until the release operator is manually released.

21. The surgical support system of claim 1 wherein the mounting element and base element abut over an area of at least four square inches.

* * * * *